United States Patent [19]

Van Dooren

[11] Patent Number: 5,131,402
[45] Date of Patent: Jul. 21, 1992

[54] METHOD AND APPARATUS FOR SIMULTANEOUSLY TAKING SAMPLES FROM BOTH THE ENDOCERVIX AND THE EXOCERVIX

[75] Inventor: Johan J. G. M. Van Dooren, Lommel, Belgium

[73] Assignee: Futurerole, Ltd., London, England

[21] Appl. No.: 642,517

[22] Filed: Jan. 17, 1991

[30] Foreign Application Priority Data

Jan. 23, 1990 [NL] Netherlands ............ 9000166

[51] Int. Cl.⁵ .................................. A61B 10/00
[52] U.S. Cl. .................................. 128/757
[58] Field of Search .................. 128/749, 757–759

[56] References Cited

U.S. PATENT DOCUMENTS

| | | | |
|---|---|---|---|
| 3,774,590 | 11/1973 | McDonald | 128/757 |
| 3,796,211 | 3/1974 | Kohl | 128/757 |
| 4,378,811 | 4/1983 | Levitan | 128/757 |
| 4,384,587 | 5/1983 | Milgrom | 128/757 |
| 4,448,205 | 5/1984 | Stenkvist | 128/757 |
| 4,700,713 | 10/1987 | Kist | 128/757 |

FOREIGN PATENT DOCUMENTS 892548 3/1962 United Kingdom ............... 128/757

*Primary Examiner*—Max Hindenburg
*Attorney, Agent, or Firm*—Kane, Dalsimer, Sullivan, Kurucz, Levy, Eisele and Richard

[57] ABSTRACT

The present invention relates to a device for simultaneously taking samples from both the endocervix and the exocervix, which device is made in one piece and includes a rod, one end of which carries a scraper. According to the invention said scraper is made with its middle part being elongated and narrow so that it may penetrate into the cervical canal for taking samples from the endocervix, whereas the remaining part is sufficiently wide to abut against the cervical wall for taking samples from the exocervix. The elongated and narrow part of the scraper is loop-shaped, whereas the remaining part is wing-shaped and located at both sides of the rod.

Furthermore the invention comprises a method for examining the cervix by means of the above mentioned device.

4 Claims, 1 Drawing Sheet

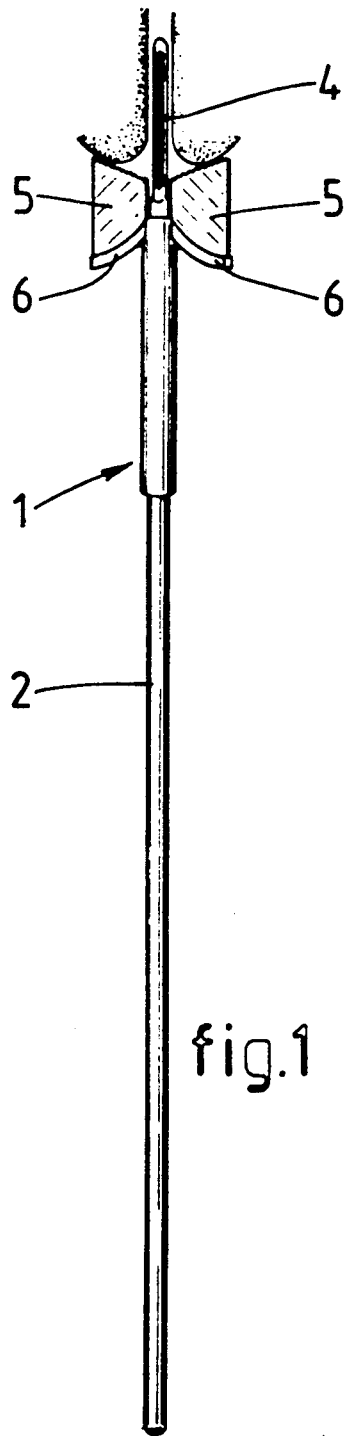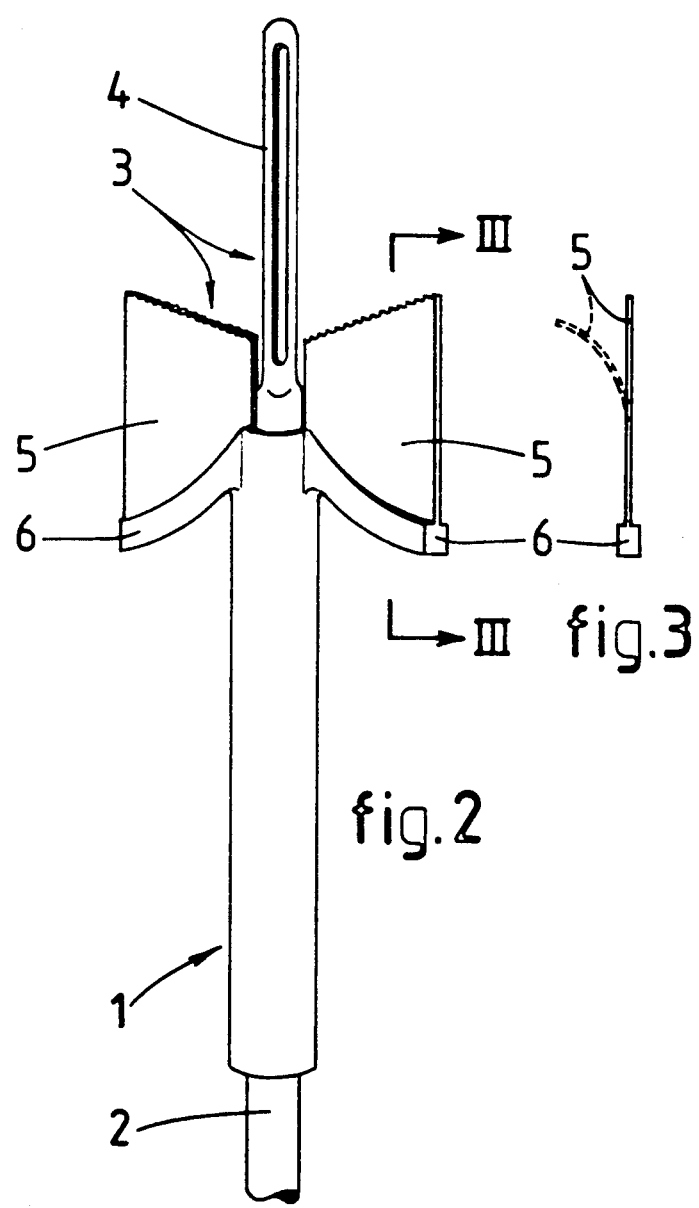

METHOD AND APPARATUS FOR SIMULTANEOUSLY TAKING SAMPLES FROM BOTH THE ENDOCERVIX AND THE EXOCERVIX

The invention relates to a device for simultaneously taking samples from both the endocervix and the exocervix, which device is made in one piece and includes a rod, one end of which carries a scraper, as well as to a method for examining the cervix.

A device and method of this kind are known from the Dutch patent application 8503596. For taking samples the known device includes a scraper consisting of parallel flexible bristles extending in parallel with the rod, each bristle having at least one longitudinally extending sharp edge for removing cells from the body cavity when the device is rotated about the axis of the rod.

The known device is disadvantageous in that introducing it into the cervical canal may be painful and furthermore there is a considerable risk of injury with all discomfort for the woman to be examined. Furthermore, when taking samples, the bristles may damage the cervical surface during rotation of the rod, causing bleeding and consequently bringing blood onto the bristles, interfering with the assay of the resulting smear.

Furthermore, there is a good chance that the cells from the cervical canal mix with the cells from the endocervix rendering a reliable examination impossible.

Another disadvantage of the known device is that with cervical canals that are less easily accessible, the central bristles cannot penetrate into the cervical canal, with the result that no samples at all are obtained from the cervical canal. Furthermore, there is the danger that the bristles not penetrating into the cervical canal may cause traumatic bleeding during the taking of samples, which is also undesirable.

The object of the invention now is to provide a device which effectively removes the above-mentioned disadvantages.

For this purpose the invention provides a device for simultaneously taking samples from both the endocervix and the exocervix, which device is made in one piece and includes a rod, one end of which carries a scraper, which scraper is made with its middle part being elongated and narrow so that it may penetrate into the cervical canal for taking samples from the endocervix, whereas the remaining part is sufficiently broad to abut against the cervical wall for taking samples from the exocervix.

The device of the invention is particularly kind in use in the sense that when introducing the device into the vagina and the cervical canal and during the taking of samples of cells and tissue, respectively, the chance of injury is minimized. Furthermore, the taking of samples is practically painless, which is of particular importance for the patient subjected to examination.

To guarantee good taking of samples in the endocervix the elongated and narrow middle part of the scraper of the invention is preferably loop-shaped. When the rod rotates about its axis, the obtained cells together with the fluid present in the cervical canal collect in the loop-shaped part. The soft wing-shaped part of the scraper is particularly suited to take cells from the exocervix without damaging it.

It is advantageous when the plane constituted by the loop-shaped part is disposed substantially at right angles to the plane constituted by the wing-shaped part, making it easier to obtain a smear from the said loop-shaped part without carrying along material from the wing-shaped part.

To improve the taking of samples by the wing-shaped part of the scraper, this part is preferably knurled or otherwise roughened at the upper side.

It is still more advantageous for taking samples from the endocervix if the wing-shaped part of the scraper is roughened at both sides.

The device is made from plastic and the narrow middle part is stiff so that it may penetrate into the cervical canal, whereas the remaining part of the scraper is soft with a stiff lower edge. Since the middle part is stiff, the cells and tissue, respectively, may be scraped more easily from the cervical canal.

Furthermore the invention relates to a method for examining the cervix, characterized in that the device of the invention is introduced into the vagina so that the narrow middle part of the scraper is inserted into the cervical canal, whereas the remaining part of the scraper abuts against the cervical wall, and rotation of the rod of the device by the sample taker causes samples of cells and tissue respectively of both the endocervix and the exocervix to collect on the scraper separate from each other after which the device is removed from the vagina for preparing a smear of the endocervix on a slide and the same of the exocervix on another slide, after which both smears are subjected to examination.

As mentioned earlier, the present invention offers a particularly elegant solution to examining the endo- and exocervix, respectively, without any appreciable chance of damaging the mucous membrane, which is obviously comfortable for the woman subjected to such an examination. The chance of bleeding occurring during examination is minimized so that bloodfree smears may be obtained which is conducive to the examination of the smears.

While a sample is taken the sample taker, usually a gynaecologist, rotates the rod a few times about its axis resulting in the samples of cells and tissue, respectively, to be taken by the scraper from both the endocervix and the exocervix, after which the device is removed from the vagina. Usually separate smears of cells, respectively tissue samples off the narrow elongated part of the scraper, i.e. from the endocervix, are then prepared on a slide, subsequently this is repeated on another slide with samples of cells and tissue, respectively, off the remaining soft part of the scraper i.e. from the exocervix.

However, it is also possible to use one slide. Although using only one slide one can still prepare smears separate from each other by putting the scraper on the slide and turning it a few times so that the smear from the endocervix is placed at the upper part of the slide and the smear of the exocervix is left on the underside of the slide. The advantage here is that one obtains two smears in one action so that fewer actions are required.

The invention will now be further explained by way of the following drawings.

FIG. 1 represents a preferred embodiment of the invention in perspective view.

FIG. 2 represents an enlarged perspective view of mainly the scraper.

FIG. 3 represents FIG. 2 along the line III—III.

In FIG. 1, 1 denotes the preferred device of the invention which is provided with a rod 2 carrying at its end a scraper 3. The scraper in this embodiment is provided with a loop-shaped part 4 which is made from plastic of such stiffness that it may easily penetrate into the cervical canal. Furthermore, the scraper is provided with a wing-shaped part 5 with base 6 at either side of the rod such that these constitute one plane. The material from which the wing-shaped part 5 is made is soft so that during rotation of the rod 2 about the axis the exocervix will not be damaged.

In this embodiment the upper side of the wing-shaped part is knurled so as to promote the taking of samples of cells and tissue respectively from the exocervix.

The scraper 3 of the invention in FIG. 2 is represented enlarged for the sake of clarity.

The wing-shaped part 5 of the scraper 3 represented in this figure may be made such that furthermore the faces of the wings at both sides are roughened for promoting the taking of samples from the exocervix. There also may be openings in the faces for promoting the taking of samples. Furthermore, the angle which the upper side of the wing-shaped part 5 of the scraper 3 makes with the rod 2 may be equal to or smaller than 90°, this angle being greater than 90° in FIG. 2.

FIG. 3 represents the position of the wing-shaped part 5 during the taking of samples and clearly shows that the wing-shaped part 5 is deflected by rotation of the rod.

It will be evident that the device of the invention is not limited to the preferred embodiment described above but that different embodiments thereof are possible which should be considered to fall within the scope of the invention.

I claim:

1. A device for simultaneously taking samples from both the endocervix and the exocervix, the device being made in one piece and comprised of a rod having a scraper at one end, the scraper having a middle part which is elongated and narrow and constructed of a material of sufficient rigidity to permit penetration into the cervical canal for taking samples from the endocervix, the middle part having a loop therethrough for capturing a sample, the loop being sufficiently narrow so that a liquid disposed therein has a high surface tension so that the sample is retained within the loop, the scraper also having wing shaped components for taking samples from the exocervix and which flank the middle part, the wing shaped components being constructed of a material which is flexible so as not to damage human tissue but which is of sufficient rigidity to permit the taking of a sample, the wing shaped components being cerrated upon the edge upon which the sample is to be taken in order to facilitate the taking of the sample.

2. The device as set forth in claim 1 wherein the middle part is disposed substantially at a right angle to the plane constituted by the wing-shaped components.

3. The device as set forth in claim 2, wherein the wing-shaped components of the scraper are knurled on their upper side.

4. Method for examining the cervix, wherein the device of claims 1, 2 and 3 is introduced into the vagina so that the narrow middle part of the scraper is inserted into the cervical canal, whereas the wing-shaped components of the scraper abut against the cervical wall, and rotation of the rod of the device by the sample taker causes samples of cells and tissue of the endocervix and the exocervix to be collected by the scraper at the middle part and upon the wing shaped components after which the device is removed from the vagina for preparing a smear of the endocervix on a slide and the same of the exocervix on another slide, after which both smears are subjected to examination.

* * * * *